United States Patent
Mace et al.

(10) Patent No.: US 10,028,978 B2
(45) Date of Patent: Jul. 24, 2018

(54) USE OF WHEY PROTEIN MICELLES FOR INFANTS AT RISK OF OBESITY OR DIABETES

(71) Applicant: NESTEC S.A., Vevey (CH)

(72) Inventors: Catherine Mace, Lausanne (CH); Lionel Jean Rene Bovetto, Lucens (CH); Etienne Pouteau, Santiago (CL)

(73) Assignee: Nestec S.A., Vevey (CH)

( * ) Notice: Subject to any disclaimer, the term of this patent is extended or adjusted under 35 U.S.C. 154(b) by 0 days.

(21) Appl. No.: 14/353,206

(22) PCT Filed: Oct. 19, 2012

(86) PCT No.: PCT/EP2012/070718
§ 371 (c)(1),
(2) Date: Apr. 21, 2014

(87) PCT Pub. No.: WO2013/057233
PCT Pub. Date: Apr. 25, 2013

(65) Prior Publication Data
US 2014/0287056 A1    Sep. 25, 2014

(30) Foreign Application Priority Data
Oct. 21, 2011 (EP) .................... 11186141

(51) Int. Cl.
*A61K 35/20* (2006.01)
*A23C 21/00* (2006.01)
*A61K 38/01* (2006.01)
*A23L 33/00* (2016.01)
*A23L 33/19* (2016.01)

(52) U.S. Cl.
CPC .............. *A61K 35/20* (2013.01); *A23C 21/00* (2013.01); *A23L 33/19* (2016.08); *A23L 33/40* (2016.08); *A61K 38/018* (2013.01); *A23V 2002/00* (2013.01)

(58) Field of Classification Search
None
See application file for complete search history.

(56) References Cited

U.S. PATENT DOCUMENTS

| | | | |
|---|---|---|---|
| 5,882,705 A * | 3/1999 | Sato et al. ................ 426/41 |
| 6,303,586 B1 * | 10/2001 | McPeak ................ A21D 2/36 |
| | | | 426/618 |
| 6,613,367 B1 * | 9/2003 | Wells ................ A61K 31/4415 |
| | | | 426/590 |
| 6,767,575 B1 | 7/2004 | Huss et al. |
| 2006/0276632 A1 * | 12/2006 | Gremlich ................ A23J 3/10 |
| | | | 530/361 |
| 2013/0171318 A1 | 7/2013 | Bovetto et al. |
| 2014/0106025 A1 | 4/2014 | Beermann et al. |
| 2016/0175393 A1 | 6/2016 | Zwijsen et al. |

FOREIGN PATENT DOCUMENTS

| WO | 2006034857 | 4/2006 |
| WO | 2006069918 | 7/2006 |
| WO | 2011112695 | 9/2011 |

OTHER PUBLICATIONS 2015 http://www.diabetes.org/diabetes-basics/genetics-of-diabetes.html.*
Cordero et al., Management of Infants of Diabetic Mothers, 1998, Arch Pediatr Adolesc Med, 152: 249-254.*
Koletzko et al., "Can infant feeding choices modulate later obesity risk?," The American Journal of Clinical Nutrition, vol. 89, No. 5 (2009), pp. 1502S-1508S.
Acheson et al., "Protein choices targeting thermogenesis and metabolism," The American Journal of Clinical Nutrition, vol. 93, No. 3, (2011), pp. 525-534.
International Search Report corresponding to related International Patent Application No. PCT/EP2012/070718 dated Jan. 3, 2013.
International Written Opinion corresponding to related International Patent Application No. PCT/EP2012/070718 dated Jan. 3, 2013.
Chile Office Action for Application No. 865-14, dated Nov. 25, 2015, 8 pages.

* cited by examiner

*Primary Examiner* — Terry A McKelvey
*Assistant Examiner* — Catheryne Chen
(74) *Attorney, Agent, or Firm* — K&L Gates LLP

(57) ABSTRACT

The invention relates to whey protein micelles for use in the treatment and/or prevention of a disorder linked to an increase in insulin secretion and/or plasma IGF-1 concentration in an infant at risk of developing obesity or diabetes. The invention also relates to a nutritional composition for infants comprising whey protein micelles. Further, the invention relates to a non-therapeutic use of a nutritional composition for infants, comprising whey protein micelles.

10 Claims, 3 Drawing Sheets

USE OF WHEY PROTEIN MICELLES FOR INFANTS AT RISK OF OBESITY OR DIABETES

CROSS REFERENCE TO RELATED APPLICATIONS

Figure 1:
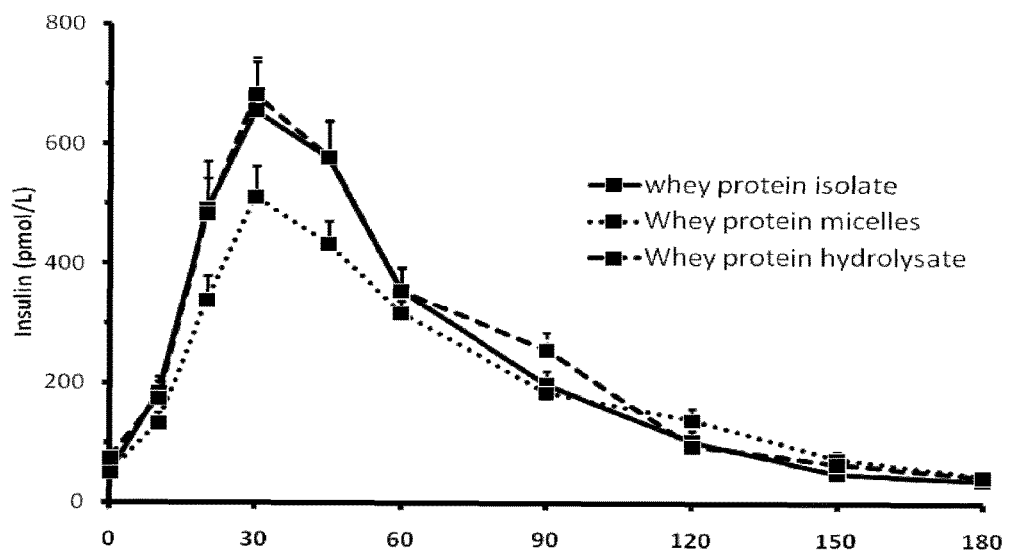

The present application is a National Stage of International Application No. PCT/EP2012/070718, filed on Oct. 19, 2012, which claims priority to European Patent Application No. 11186141.5, filed Oct. 21, 2011, the entire contents of which are being incorporated herein by reference.

The present invention relates to whey protein micelles for use in the treatment and/or prevention of a disorder linked to an increase in insulin secretion and/or plasma IGF-1 concentration in an infant at risk of developing obesity or diabetes. Particularly, the invention relates also to a nutritional composition for infants comprising whey protein micelles.

Mother's milk is recommended for all infants. However, in some cases breast feeding is inadequate or unsuccessful or inadvisable for medical reasons or the mother chooses not to breast feed. Infant formulas have been developed for these situations.

The prevalence of obesity and overweight in adults, children and adolescents has increased rapidly over the past 30 years in the United States and globally and continues to rise. Overweight and obesity are classically defined based on the percentage of body fat or, more recently, the body mass index or BMI. The BMI is defined as the ratio of weight in Kg divided by the height in meters, squared. As overweight and obesity become more prevalent in all age groups, it is inevitable that the number of women giving birth who are also overweight or obese will increase. It is known that overweight and obese women who become pregnant have a greater risk of developing gestational diabetes. Maternal hyperglycaemia may lead to infants with increased body size and fat mass and such infants are themselves prone to develop obesity and diabetes later in childhood or in adult life. Moreover, recent research has suggested that obese women who themselves have normal glucose tolerance give birth to infants with a higher fat mass than those born to women who are not obese.

An increasing weight of scientific evidence suggests that infants born to overweight and obese mothers have a greater risk of becoming overweight or obese later in life than infants born to mothers who are not overweight or obese. This predisposition appears to be higher if both parents are affected. Childhood overweight and obesity currently affects 18 million children under age 5 worldwide. Almost 30% of US children and adolescents and between 10 and 30% of European children are overweight or obese.

Low birth weight, resulting from intra-uterine growth retardation (IUGR) or prematurity, is often compensated by accelerated post-natal growth (catch-up growth) and is considered to be an important risk factor for the later development of metabolic disease such as type-2 diabetes, obesity, hypertension and ischemic heart disease (Baker et al. 1993, Hales et al. 1991). Catch-up growth is most often characterized by hyperinsulinemia (i.e. insulin resistance) and a disproportionately higher rate of fat gain relative to lean tissue ("catch-up fat"), which are viewed to be of central importance in the mechanisms by which catch-up growth predisposes to obesity, type-2 diabetes and cardio vascular disease (CVD) later in life (Meas T. (2010), Fetal origins of insulin resistance and the metabolic syndrome: a key role for adipose tissue? Diabetes Metab 36, 11-20).

WO2006/069918 discloses a method of continuously reducing the circulating level of insulin like growth factor 1 (IGF-1) in the first few months of the life of an infant by administering to an infant in need thereof a therapeutic amount of a nutritional composition comprising less than 2.25 g of proteins per 100 kcal. As IGF-1 is known to be a key control point in nutritional regulation of growth, this may offer a method of reducing the risk of developing obesity later in life.

WO2008/071667 discloses a nutritional composition for infants at risk of developing obesity later in life comprising a protein content of less than 1.8 g per 100 kcal and having a total energy density of less than 650 kcal per liter.

WO2011/112695 discloses health benefits provided by whey proteins including control of blood glucose such that they are suitable for diabetics.

Thereby, it has been realized that the total protein quantity provided to an infant can be reduced whilst still meeting the minimum requirement for essential amino acids, and this by a judicious selection of protein sources supplemented if necessary by small quantities of free amino acids.

There is, however, still a persisting need in the food industry to find alternatives or better solutions, which for example do not require reducing the nutritionally important total protein content of a formula, to address the nutritional needs of these at risk infants whilst reducing their risk of developing obesity and/or diabetes later in life.

For small birth weight infants and IUGR infants who need to catch-up in terms of growth and brain development, a higher protein intake is required through specialized formula or supplemented human milk. Therefore, there is a need in the food industry to find alternatives or better solutions, which for example provide a higher protein content of a high nutritional quality protein of a formula allowing a healthy catch-up growth of small birth weight infants and/or IUGR infants, i.e. providing a linear growth and brain development for those infants but without an excess of body fat deposition and hyperinsulinemia.

The object of the present invention is to improve the state of the art and to provide a new and improved solution of addressing disorders linked to an increase in insulin secretion and/or plasma IGF-1 concentration in infants at risk of developing obesity or diabetes, and/or to overcome at least some of the inconveniences described above.

The object of the present invention is achieved by the subject matter of the independent claims. The dependent claims further develop the idea of the present invention.

Accordingly, the present invention provides in a first aspect whey protein micelles for use in the treatment and/or prevention of a disorder linked to an increase in insulin secretion and/or plasma IGF-1 concentration in an infant at risk of developing obesity or diabetes.

In a second aspect, the invention relates to a nutritional composition for infants comprising whey protein micelles. Particularly, the invention relates to a nutritional composition for infants for use in the treatment and/or prevention of a disorder linked to an increase in insulin secretion and/or plasma IGF-1 concentration, wherein the nutritional composition comprises whey protein micelles.

In a still further aspect, the invention pertains to a non-therapeutic use of a nutritional composition for infants comprising whey protein micelles, to decrease insulin secretion and/or plasma IFG-1 concentration in healthy infants.

"Whey protein micelles" are defined herein as described in EP1839492A1. Particularly, the "whey protein micelles"

are the micelles comprised in the whey protein micelles concentrate obtainable by the process as disclosed in EP1839492A1. Therein, the process for the production of whey protein micelles concentrate comprises the steps of: a) adjusting the pH of a whey protein aqueous solution to a value between 3.0 and 8.0; b) subjecting the aqueous solution to a temperature between 80 and 98° C.; and c) concentrating the dispersion obtained in step b). Thereby, the micelles produced have an extremely sharp size distribution, such that more than 80% of the micelles produced have a size smaller than 1 micron in diameter and preferably are between 100 nm and 900 nm in size. The "whey protein micelles" can be in liquid concentrate or in powder form. Importantly, the basic micelle structure of the whey proteins is conserved, in the concentrate, the powder and reconstituted from the powder for example in water. The "whey protein micelles" are physically stable in dispersion, as powder as well as during spray-drying or freeze-drying.

"Infant" means a child under the age of 36 months.

"Infant at risk of developing obesity or diabetes" is an infant with a predisposition of becoming overweight or obese and/or developing diabetes later in life. Such a predisposition can be due to genetic factors of the infant and/or due to the fact that the infant has suffered of IUGR or is born to an overweight, obese or diabetic mother. The predisposition may be even higher if both parents of the infant are affected.

"Insulin" is a hormone secreted by the beta cells of the pancreas in response to a meal. Insulin is central to regulating carbohydrate and fat metabolism in the body.

"IGF-1" is Insulin-like Growth Factor 1, also known as somatomedin C or mechano growth factor. It is a protein that in humans is encoded by the IGF1 gene. IGF-1 is a hormone similar in molecular structure to insulin. It is produced primarily by the liver and insulin is a positive regulator of IGF-1 secretion. IGF-1 plays an important role in infant and childhood growth. In addition to promoting growth, increases in plasma IGF-1 levels may stimulate adipogenic activity and adipocyte differentiation, potentially increasing the susceptibility to overweight and obesity at a later age.

"Plasma IGF-1 concentration" is the level of IGF-1 in blood plasma. IGF-1 secretion is stimulated by insulin. Today, infants fed with a standard infant formula are known to have a postprandial plasma concentration of insulin and IFG-1 higher than breastfed infants. For instance, at the age of 4 months, standard formula fed infants have a plasma insulin concentration of 11.3 mU/l versus 3.5 mU/l ($p<0.0001$) for breastfed infants, and a plasma IGF-1 concentration of 67.1±20.8 µg/ml versus 48.1±15.6 µg/ml ($p<0.0001$).

A high insulinogenic nutrition represents a chronic stimulus to the beta cells that may induce an adaptive hypertrophy and a progressive dysregulation of the cells, resulting in postprandial hyperinsulinemia. Postprandial hyperinsulinemia may promote weight gain, fat deposition and the development of insulin resistance, metabolic syndrome, glucose intolerance and type-2 diabetes (Kopp W., Metabolism. 2003, July; 52(7):840-844).

"Overweight" is defined for an adult human as having a BMI between 25 and 30. Thereby, BMI (body mass index) means the ratio of weight in kg divided by the height in meters, squared.

"Obesity" is a condition in which the natural energy reserve, stored in the fatty tissue of animals, in particular humans and other mammals, is increased to a point where it is associated with certain health conditions or increased mortality. "Obese" is defined for a human as having a BMI greater than 30.

It has been surprisingly found by the inventors, that whey protein micelles consumed as part of a meal significantly decrease the postprandial response of plasma insulin in comparison to a same, iso-caloric and iso-nitrogenous, meal comprising whey protein isolates (WPI) or extensively hydrolyzed whey proteins (EHWP) instead of the whey protein micelles in a human subject. The results of the clinical study are disclosed in the Example section. Consequently, a decrease of plasma insulin and consequently IGF-1 levels in an infant after consumption of an infant feeding formula comprising whey protein micelles will situate the plasma insulin concentration as well as the plasma IGF-1 concentration of said infant much closer to the one of a breastfed infant. The infant will have a reduced risk of developing obesity, insulin resistance, metabolic syndrome, glucose intolerance, type-2 diabetes etc. later in life.

Although not wishing to be bound by theory, the inventors think that whey protein micelles as part of a meal seem to delay gastric emptying or to be more slowly digested as compared to native whey proteins such as WPI or hydrolyzed whey proteins (EHWP). Thereby, whey protein micelles deliver the amino acids more slowly into the peripheral blood circulation. This lower amino acidemia is concomitant with a reduced insulinemia compared to e.g. WPI or dairy protein hydrolysates.

FIG. 1: Plasma concentrations of insulin 3 h after the ingestion of the 3 meal replacements in healthy human subjects.

Figure 2:
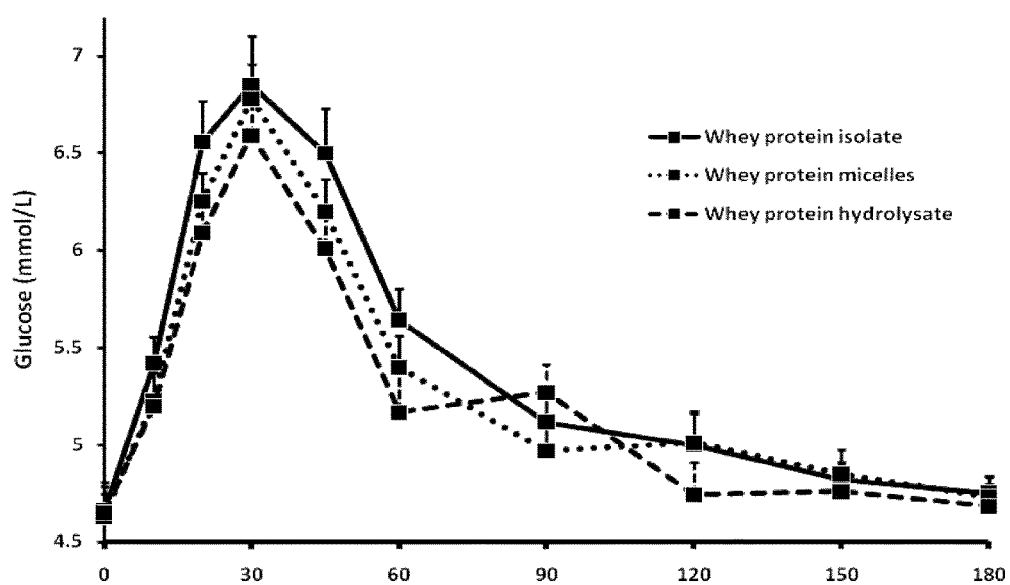

FIG. 2: Plasma concentrations of glucose 3 h after the ingestion of the 3 meal replacements in healthy human subjects.

Figure 3:
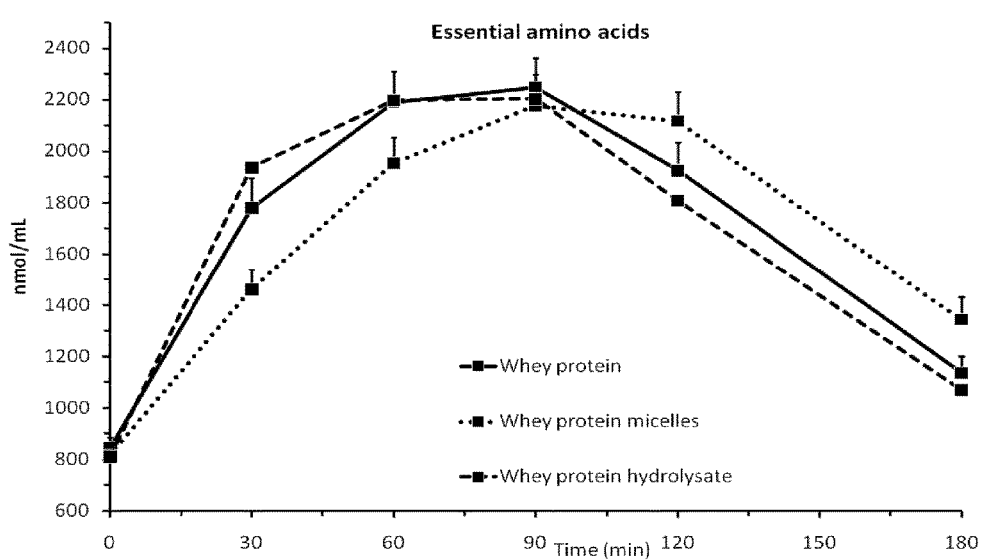

FIG. 3: Plasma concentrations of essential amino acids 3 h after the ingestion of the 3 meal replacements in healthy human subjects.

The present invention pertains to whey protein micelles for use in the treatment and/or prevention of a disorder linked to an increase in insulin secretion and/or plasma IGF-1 concentration in an infant at risk of developing obesity or diabetes. The disorder may be selected from the group consisting of obesity, insulin resistance, metabolic syndrome, glucose intolerance and type-2 diabetes.

For example the disorder may also be selected from the group consisting of insulin resistance, metabolic syndrome, glucose intolerance and type-2 diabetes.

The mechanisms by which growth patterns in infancy may affect obesity risks later in life are not completely understood. A role for insulin and insulin-like growth factor 1 (IGF-1) has been proposed (Koletzko B, von Kries R, Closa R, et al. Can infant feeding choices modulate later obesity risk? Am J Clin Nutr 2009; 89:1502S-8S). In addition to promoting growth, increases in these hormones could stimulate adipogenic activity and adipocyte differentiation thereby increasing susceptibility to overweight and obesity at a later age.

The whey protein micelles of the invention are to be administered to the infant from birth to the age of 36 months.

In a preferred embodiment, the whey protein micelles for use according to the invention constitute at least 30% of the protein source of the infant's daily diet. Thereby, preferably at least 40%, and more preferably at least 50% of the protein source are whey protein micelles. Advantageously and in order to be most effective, a good part of the infant's daily protein source are whey protein micelles.

In a further aspect, the invention relates to a nutritional composition for infants for use in the treatment and/or prevention of a disorder linked to an increase in insulin secretion and/or plasma IGF-1 concentration, wherein the nutritional composition comprises whey protein micelles, and wherein the disorder is selected from the group consisting of obesity, insulin resistance, metabolic syndrome, glucose intolerance and type-2 diabetes.

In a preferred embodiment, the nutritional composition of the invention further comprises casein. The advantages of adding casein to the nutritional composition is to better mimic human milk. The human milk composition starts with a whey-to-casein ratio of about 80:20 to decrease to about 50:50 in very mature milk. Mimicking human milk brings several advantages on having a closer amino acid composition to human milk, on improving thereby the health benefits, the energy balance, the taste and possibly the product stability. Preferably, the nutritional composition comprises casein, wherein the whey-to-casein weight ratio is between 80:20 and 20:80, or between 70:30 and 30:70, or between 60:40 and 40:60.

In an alternative embodiment, the nutritional composition comprises whey protein micelles in a range from 80% to 100% of the total protein content of the nutritional composition. Such compositions contain a higher amount of whey proteins as can typically be found in standard infant formulae. The nutritional composition thereby comes closer in its milk protein composition to early phase human milks. Advantageously, such nutritional compositions are provided to pre-term born infants and/or infants suffering from IUGR.

The nutritional composition of the invention has a total protein content ranging from 1.4 to 3.8 g per 100 kcal.

A further aspect of the invention is a non-therapeutic use of a nutritional composition for infants comprising whey protein micelles, to decrease insulin secretion and/or plasma IFG-1 concentration in a healthy infant.

It is an advantage of the present invention that a nutritional composition comprising whey protein micelles can also be administered to infants who are healthy and/or are not at risk of developing obesity or diabetes later in life. In fact, the nutritional composition as disclosed herein provides also healthy formula-fed infants with a lower plasma insulin and IGF-1 concentration in comparison with infants fed a standard infant formula. Thereby, the nutritional health and hormonal status of infants fed a whey protein micelles comprising composition is closer to breastfed infants than those fed a traditional, standard infant formula. It is well recognized today that human milk is still the best nutrition for infants and serves as 'gold standard' for all developments of new infant nutrition. So far, however, no infant formula is capable of fully mimicking postprandial plasma concentrations of insulin and fasting plasma concentrations of IGF-1 to the concentrations observed in breastfed infants. The nutritional composition of the invention is a step closer to the 'gold standard'.

Further, the invention relates to an infant feeding formula comprising whey protein micelles.

Particularly, the invention relates to an infant feeding formula comprising whey protein micelles, wherein the content of whey protein micelles ranges from 0.4 to 3.8 g per 100 kcal, preferably from 0.8 to 2.7 g per 100 kcal.

Those skilled in the art will understand that they can freely combine all features of the present invention disclosed herein. In particular, features described for the therapeutic use of the whey protein micelles may be combined with the therapeutic and non-therapeutic uses of the nutritional compositions and vice versa. Further, features described for different embodiments of the present invention may be combined. Further advantages and features of the present invention are apparent from the figures and examples.

EXAMPLE

A randomized double-blinded crossover study was performed in twenty-three healthy human subjects. The subjects ingested different meal replacements at lunch time, followed by a wash-out period of one week. A catheter was inserted in the arm of the subjects and served for collecting arterialized blood postprandial for 3 h. Plasma from the blood samples was used to analyze hormones (insulin, c-peptide and glucagon), glucose and amino acids.

The 3 meal replacements tested were iso-caloric and iso-nitrogenous. They were composed of the tested protein (30 g, 7.2% w/w), lipids (11.7 g, 2.8% w/w), carbohydrates (42.7 g, 10.2% w/w) and fibers (6.3 g, 1.5% w/w). The tested proteins were: (1) whey protein isolates (WPI); (2) whey protein micelles (WPM); and (3) extensively hydrolyzed whey protein (EHWP). The meal replacements were completed with water to 420 mL and contained 388 kcal as energy intake.

The results showed a significant decrease of the Cmax (maximal concentration, P=0.015) of insulin responses after the ingestion of the WPM compared with the WPI and EHWP meal replacements. FIG. 1 showed the postprandial insulin responses after the meal replacement ingestion. The postprandial responses of glucose were similar between the meal replacements (FIG. 2). Surprisingly, the WPM meal replacement induced the lowest concentration of plasma amino acids 30 min after the meal ingestion, as opposed to the other protein meals (FIG. 3). The WPM exhibited the lowest rate of appearance of amino acids (especially essential amino acids) in the systemic blood circulation. These lowest plasma amino acids probably participate in lowering the plasma insulin, c-peptide and glucagon (not shown) responses of the WPM at 30 min, the time of insulin Cmax.

FIG. 1-3: small dotted lines represent the whey protein micelles.

This study shows an advantage of WPM in lowering plasma insulin and other hormone compared with WPI in healthy human subjects.

The invention claimed is:

1. A method for the treatment of a disorder linked to an increase in insulin secretion and/or plasma IGF-1 concentration in an infant at risk of developing obesity or diabetes, the method comprising:
    administering to the infant a composition comprising whey protein micelles, wherein the whey protein micelles constitute at least 30% of the protein source of the infant's daily diet, wherein a protein content of the composition ranges from 1.4 to 3.8 g per 100 kcal, and wherein the composition decreases insulin responses after ingestion of a meal relative to a composition containing an equal amount of whey protein isolates or whey protein hydrolysates.

2. The method according to claim 1, wherein the disorder is selected from the group consisting of obesity, insulin resistance, metabolic syndrome, glucose intolerance and type-2 diabetes.

3. The method according to claim 1, wherein the infant is from birth to the age of 36 months.

4. A method for the treatment of a disorder linked to an increase in insulin secretion and/or plasma IGF-1 concentration in an infant age 0-36 months, the method comprising:

administering to the infant whey protein micelles, wherein the whey protein micelles constitute at least 30% of the protein source of the infant's daily diet, wherein a protein content of the composition ranges from 1.4 to 3.8 g per 100 kcal, and wherein the whey protein micelles decrease insulin responses after ingestion of a meal relative to a composition containing an equal amount of whey protein isolates or whey protein hydrolysates.

5. The method according to claim 4, wherein the disorder is selected from the group consisting of obesity, insulin resistance, metabolic syndrome, glucose intolerance and type-2 diabetes.

6. The method according to claim 4, further comprising administering casein.

7. The method according to claim 6, wherein the whey-to-casein weight ratio is between 80:20 and 40:60.

8. The method according to claim 4, wherein the whey protein micelles constitute from 80 to 100% of a protein content of a nutritional composition administered to the infant.

9. A method of decreasing insulin secretion and/or plasma IFG-1 concentration in an infant in need thereof, the method comprising:
administering to the infant a composition comprising whey protein micelles to the infant wherein the whey protein micelles constitute at least 30% of the protein source of the infant's daily diet, wherein a protein content of the composition ranges from 1.4 to 3.8 g per 100 kcal, and wherein the composition decreases insulin responses after ingestion of a meal relative to a composition containing an equal amount of whey protein isolates or whey protein hydrolysates.

10. The method of claim 1, wherein the infant is an infant born to an obese, overweight, or diabetic mother.

* * * * *